United States Patent [19]

Cheney, II et al.

[11] Patent Number: 5,391,250
[45] Date of Patent: Feb. 21, 1995

[54] METHOD OF FABRICATING THIN FILM SENSORS

[75] Inventors: Paul S. Cheney, II, Beverly Hills; William P. Van Antwerp, Los Angeles, both of Calif.

[73] Assignee: MiniMed Inc., Sylmar, Calif.

[21] Appl. No.: 212,961

[22] Filed: Mar. 15, 1994

[51] Int. Cl.6 .................... B29C 65/00; B32B 31/00
[52] U.S. Cl. ................... 156/268; 156/286; 156/290
[58] Field of Search ............... 156/286, 290, 306.6, 156/297, 268, 60, 631, 632, 638; 428/901; 128/637; 204/403; 29/846

[56] References Cited

U.S. PATENT DOCUMENTS

| | | | |
|---|---|---|---|
| 2,899,658 | 8/1959 | Bean, Jr. | 156/297 |
| 4,104,099 | 8/1978 | Scherrer | 156/306.6 |
| 4,897,173 | 1/1990 | Nankai et al. | 204/403 |
| 5,108,819 | 4/1992 | Heller et al. | |
| 5,196,088 | 3/1993 | Soda | 156/631 |

*Primary Examiner*—Michael W. Ball
*Assistant Examiner*—Richard Crispino
*Attorney, Agent, or Firm*—Kelly Bauersfeld & Lowry

[57] ABSTRACT

An improved method is provided for making thin film electrochemical sensors, such as subcutaneous glucose sensors used to monitor blood glucose levels in a diabetic patient. The fabrication method comprises placing a thin film base layer of insulative material onto a rigid flat substrate, with a curable adhesive interposed between the perimeter of the base layer and substrate to define a shallow cavity underlying a central portion of the base layer. The subassembly is subjected to heat and pressure to cure the adhesive, resulting in air expulsion from the cavity such that the central portion of the base layer is drawn into intimate contact with the substrate. Appropriate conductor elements for one or more sensors are formed on the base layer as by conventional contact mask photolithography, and a thin film cover layer of insulative material is applied thereover with apertures in the cover layer exposing distal end sensor electrodes and proximal end contact pads. The insulative cover and base layers are then cut along a line surrounding each finished sensor which is lifted and separated easily from the substrate.

13 Claims, 4 Drawing Sheets

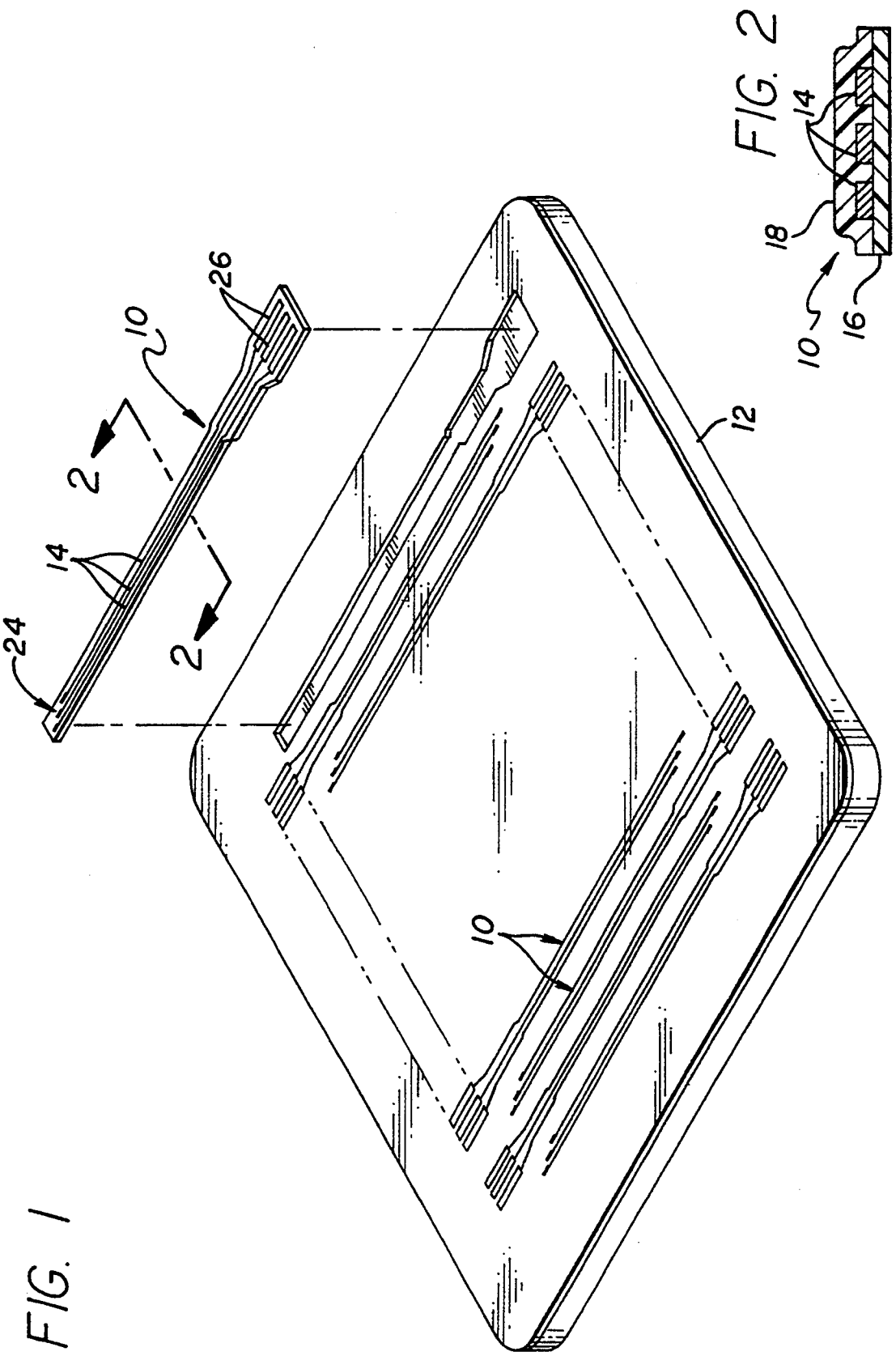

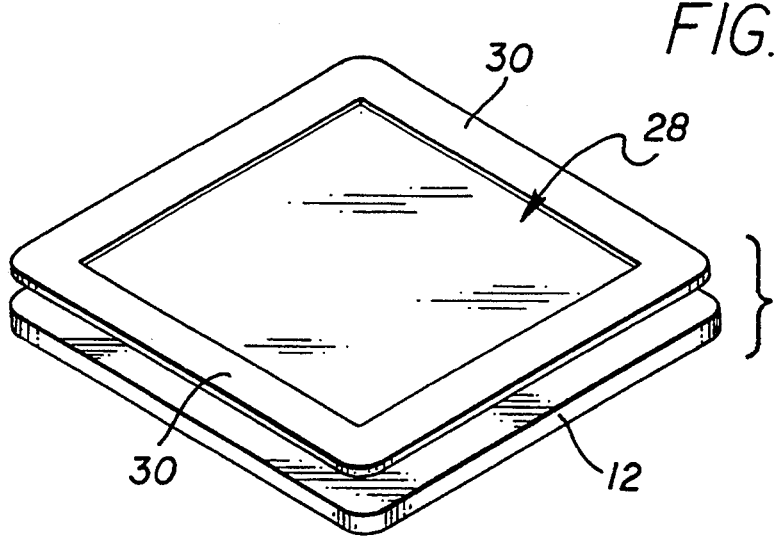
FIG. 3
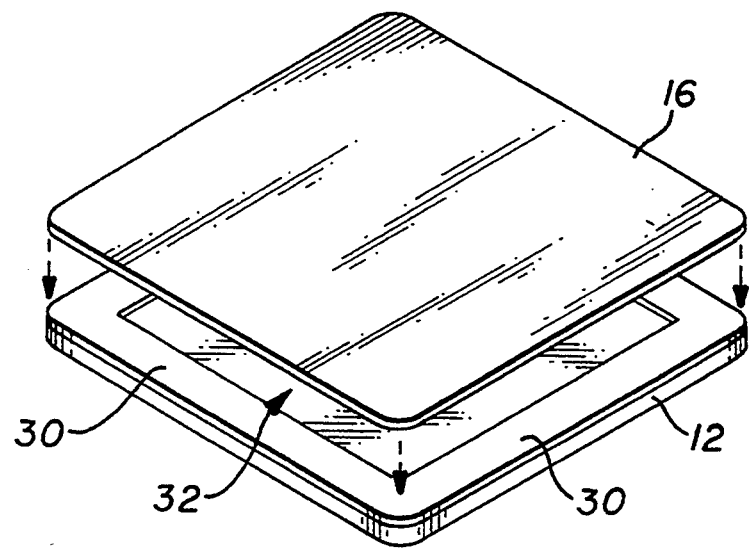
FIG. 4
FIG. 5
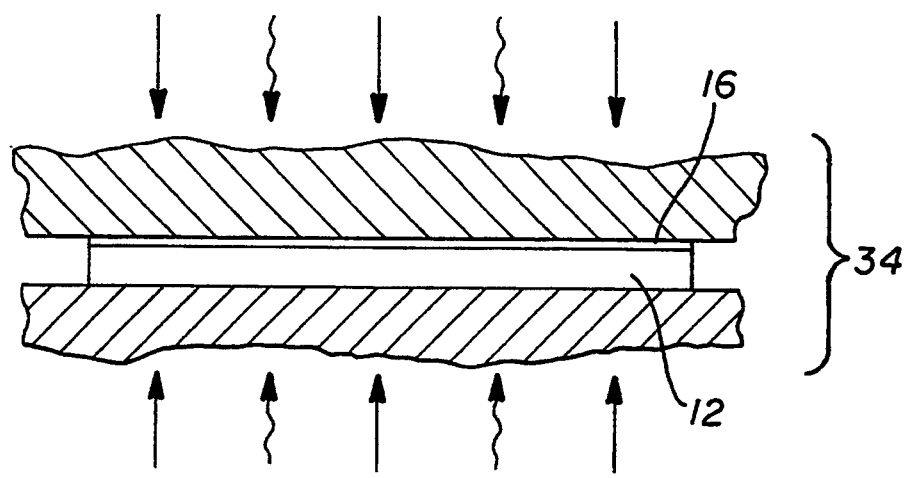

METHOD OF FABRICATING THIN FILM SENSORS

BACKGROUND OF THE INVENTION

This invention relates generally to fabrication methods for producing thin film electrochemical sensors of the type used, for example, in subcutaneous or transcutaneous monitoring of blood glucose levels in a diabetic patient. More specifically, this invention relates to an improved fabrication method wherein thin film sensors are formed on a rigid flat substrate by contact mask photolithography or the like, without requiring attachment of the sensors to the substrate.

Thin film electrochemical sensors are generally known in the art for use in a variety of specialized sensor applications. Such thin film sensors generally comprise one or more thin conductors applied by photolithography mask and etch techniques between thin layers of a nonconductive film material, such as polyimide film. The conductors are shaped to define distal end sensor tips having an appropriate electrode material thereon, in combination with proximal end contact pads adapted for conductive connection with appropriate electronic monitoring equipment. In recent years, thin film sensors of this general type have been proposed for use as a transcutaneous sensor in medical applications. As one example, thin film sensors have been designed for use in monitoring blood glucose levels in a diabetic patient, with the distal end sensor electrodes positioned subcutaneously in direct contact with patient blood.

In accordance with known photolithographic fabrication techniques, thin film sensors have been produced by sequential buildup of the sensor layers on a flat and rigid substrate, such as a glass plate. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic mask and etch steps to form the conductors. A cover layer of insulative material is then applied, and the resultant sensors are stripped from the substrate. However, this stripping step must be performed carefully in order to separate the finished sensors from the substrate without damage. Unfortunately, the initial step of spin forming the base layer on the substrate causes the base layer to be firmly adhered to the substrate, such that separation of the finished sensors from the substrate is both costly and time consuming, thereby undesirably increasing the manufactured cost of thin film sensors.

There exists, therefore, a need for improvements in methods for producing thin film electrochemical sensors, particularly with respect to reducing sensor production time and cost by facilitating removal of finished sensors from a flat substrate. The present invention fulfills these needs and provides further related advantages.

SUMMARY OF THE INVENTION

In accordance with the invention, an improved fabrication method is provided for producing thin film electrochemical sensors. The method comprises the formation of one or more sensors on a flat and rigid substrate, such as a glass plate, by means of contact mask lithography or the like, but without requiring physical attachment of the sensors to the substrate. In the invention, a base layer of insulative material is vacuum drawn into intimate contact with the substrate to provide a flat and stable surface upon which remaining components of the thin film sensors can be applied by photolithographic techniques. The finished sensors can then be removed quickly and easily from the substrate.

In accordance with the preferred form of the invention, a thin film base layer of insulative material such as polyimide sheet is placed onto the flat and rigid substrate, with a thin die-cut sheet or frame of a curable adhesive such as an epoxy resin disposed between the perimeter of the overlying base layer and the underlying substrate, thereby defining a shallow cavity underlying a central portion of the base layer. This subassembly is subjected to appropriate heat and pressure to cure the adhesive. Air and other gaseous constituents within the cavity are driven therefrom during this cure step, to create a vacuum within the cavity. As a result, the central portion of the base layer is vacuum drawn into intimate seated contact upon the flat substrate. The cured adhesive provides a barrier to post-cure return flow of gases into the cavity, such that the central portion of the base layer is retained on the substrate in a uniformly flat orientation.

Subsequently, the remaining components of one or more thin film sensors are applied to the base layer, preferably by photolithographic mask and etch techniques. For example, a thin conductive film is applied to the base layer by electrodeposition, sputtering, etc. The conductive film is appropriately masked and etched to define elongated conductor traces for one or more sensors. The conductor traces are in turn covered by a thin film cover layer of insulative material, such as a photoimagable polyimide suitable for masking and exposure to form apertures therein to expose distal end sensor tips and proximal end contact pads. Electrode chemistries are applied to the sensor tips, such as glucose oxidase for use in monitoring glucose blood levels. The thus-formed sensors are removed from the substrate by cutting the cover and base layers along a line surrounding each finished sensor, whereupon each sensor can then be lifted and separated easily from the underlying substrate.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an exploded perspective view illustrating a plurality of thin film electrochemical sensors formed on a rigid flat substrate;

FIG. 2 is an enlarged cross sectional view taken generally on the line 2—2, of FIG. 1;

FIG. 3 is a perspective view illustrating application of a die-cut strip of curable adhesive to the perimeter of the substrate;

FIG. 4 is an exploded perspective view showing placement of a thin film base layer onto the substrate;

FIG. 5 is a somewhat schematic representation of a cure step for curing the adhesive interposed between the base layer and substrate;

DETAILED DESCRIPTION OF THE PREFERRED EMBODIMENT

Figure 6:
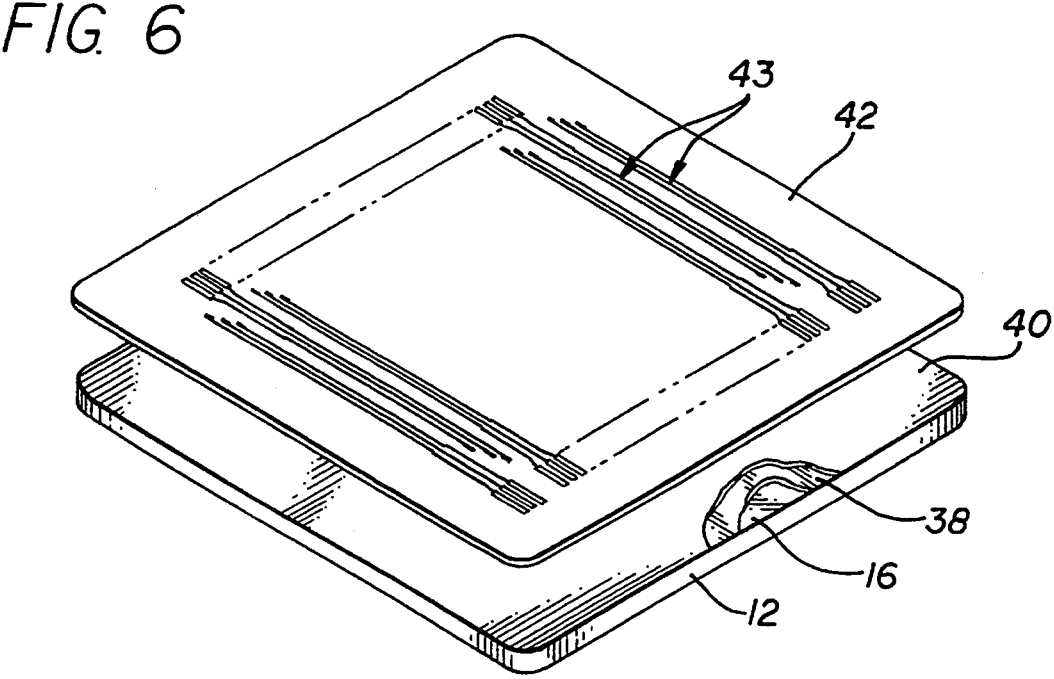
FIG. 6 is an exploded perspective view, with portions broken away, illustrating photolithographic mask and etch steps for forming conductive sensor traces on the base layer.

As shown in the exemplary drawings, an improved fabrication method is provided for producing thin film electrochemical sensors referred to generally by the reference numeral 10 in FIG. 1. One or more sensors 10 are formed on a rigid flat substrate 12, such as a glass plate. The sensors 10 are formed in a manner which is compatible with photolithographic mask and etch techniques, but wherein the sensors are not physically adhered or attached directly to the substrate 12. Accordingly, finished sensors 10 can be removed quickly and easily from the substrate by simple lift-off separation.

Figure 10:
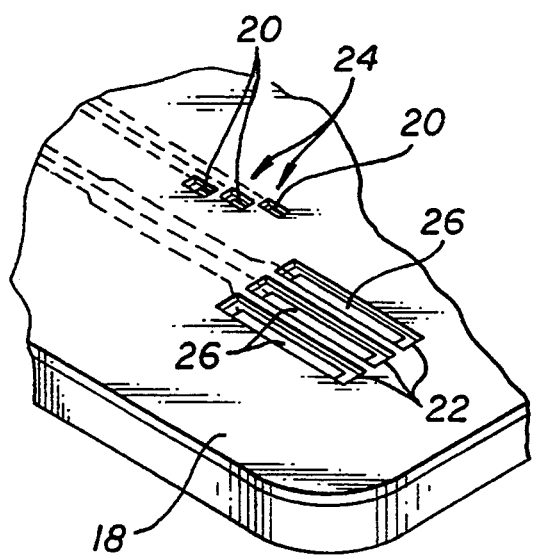
FIG. 10 is an enlarged fragmented perspective view illustrating sensor contact pad and distal end electrodes exposed through the insulative cover layer.

The electrochemical sensors 10 shown in the accompanying drawings are particularly designed for use as subcutaneous or transcutaneous glucose sensors for monitoring blood glucose levels in a diabetic patient. Each sensor comprises a plurality of elongated thin film conductors 14 formed between an underlying insulative thin film base layer 16 (FIG. 2) and an overlying insulative thin film cover layer 18. Apertures 20 and 22 (FIG. 10) are formed in the cover layer 18 to expose distal end electrodes 24 and proximal end contact pads 26. In a glucose monitoring application, the thin film sensor 10 is placed transcutaneously so that the distal end electrodes 24 are in direct contact with patient blood or extracellular fluid, and wherein the contact pads 26 are disposed externally for convenient connection to a monitoring device (not shown).

The substrate 12 comprises a rigid and flat structure suitable for use in photolithographic mask and etch processes. In this regard, the substrate 12 defines an upper surface 28 (FIG. 3) having a high degree of uniform flatness. A polished glass plate may be used defining the smooth upper surface 28. Alternative substrate materials include, for example, stainless steel, aluminum, and plastic materials such as Delrin, etc.

A thin layer film 30 of a curable adhesive, provided as shown in the form of a die-cut strip or frame, is applied in a closed loop pattern to the perimeter of the substrate 12, as viewed in FIG. 3. The base layer 16 is then placed on the substrate 12, with a perimeter of the base layer 16 in intimate seated contact upon the adhesive strip 30. The thus-assembled components define a shallow cavity 32 between a central portion of the base layer 16 and the underlying substrate 12, with the adhesive strip 30 circumscribing the peripheral edge of the cavity 32. In a preferred form, the base layer 16 comprises a thin film sheet of insulative material, such as polyimide having a film thickness on the order of about 0.003 inch. The adhesive strip 30 comprises an epoxy resin which may be impregnated with fiberglass, such as an epoxy resin available from 3M Aerospace Division of Springfield, Mo., under the name AF-163-205T. Alternative adhesive materials may include ultraviolet curable adhesives, etc. Moreover, if desired for improved adhesion between the base layer 16 and the adhesive strip 30, a perimeter region of the base layer may be surface etched.

The subassembly including the base layer 16 and substrate 12 are subjected to a curing step as viewed schematically in FIG. 5. As shown, these components are placed in a press 34 and subjected to appropriate heat and pressure to cure the adhesive material 30. During this cure step, air and other gaseous constituents are expelled from the cavity 32, resulting in an effective vacuum therein which draws the central portion of the base layer 16 downwardly into intimate and uninterrupted surface-to-surface engagement with the flat upper surface 28 of the substrate 12. When the adhesive material 30 reaches a substantially cured state, return ingress of gaseous constituents to the cavity 32 is prevented, whereby the central portion of the base layer 16 is retained in intimate engagement with the substrate.

FIG. 6 illustrates photolithographic steps for forming conductive sensor traces on the insulative base layer 16. More specifically, the base layer 16 is initially coated with a thin film conductive layer 38 by electrode deposition, surface sputtering, or other suitable process step. In the preferred form, this conductive layer 38 may be provided as a plurality of thin film conductive layers, such as an initial chrome-based layer suitable for chemical adhesion to the polyimide base layer 16, followed by subsequent formation of thin film gold-based and chrome-based layers in sequence.

Figure 7:
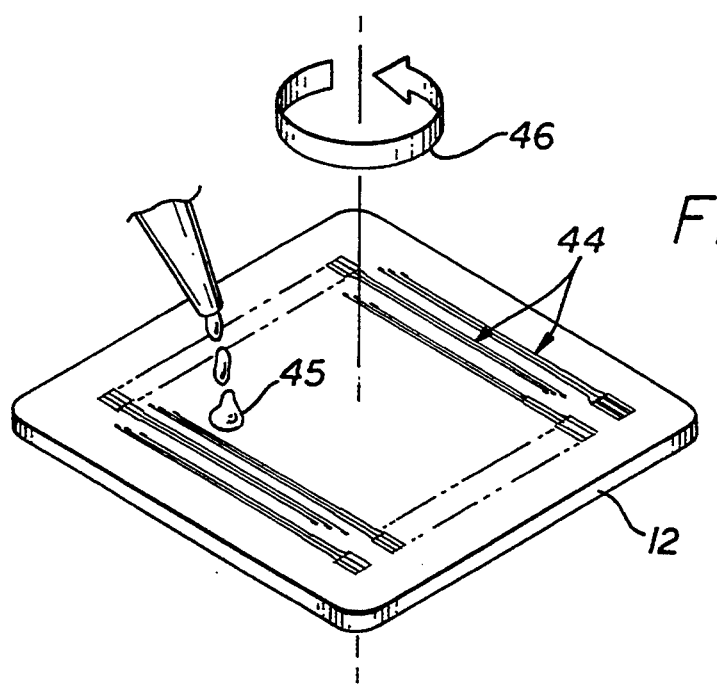
FIG. 7 is a perspective view illustrating application of a thin film cover layer over the conductive sensor traces.

The conductive layer 38 is then covered, in accordance with conventional photolithographic techniques, with a selected photoresist coating 40, and a contact mask 42 is applied over the photoresist coating 40 for suitable photoimaging. The contact mask includes one or more conductor trace patterns 43, such as the plurality of traces shown in FIG. 6 in closely nested relation, for appropriate exposure of the photoresist coating 40, followed by an etch step resulting in a plurality of conductive sensor traces 44 remaining on the base layer 16, as shown in FIG. 7. In the illustrative sensor construction designed for use as a subcutaneous glucose sensor, each sensor trace is shown to include three parallel conductors 14 corresponding with three separate electrodes 24 as will be described.

Figure 8:
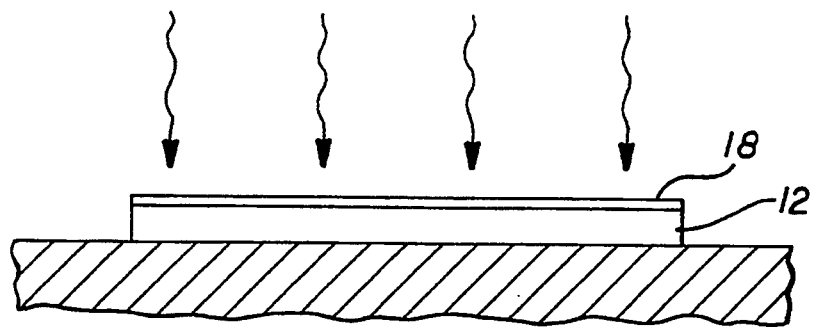
FIG. 8 is a schematic representation of a cure step for curing the cover layer.

The conductive sensor traces 44 are covered by the thin film cover layer 18 of insulative material. This step is shown in FIG. 7 by applying liquid-based insulative material 45 over the sensor traces 44, and then spinning the substrate 12 as indicated by arrow 46 to distribute the liquid material 45 as a thin film overlying the sensor traces 44 and extending beyond the marginal edges of the sensor traces in sealed contact with the base layer. This liquid material is then subjected to a suitable radiation and/or heat cure step as shown in FIG. 8. Various cover layer materials may be used, with a preferred material comprising a photoimagable polyimide available from OCG, Inc. of West Paterson, N.J., under the product number 7020.

Figure 9:
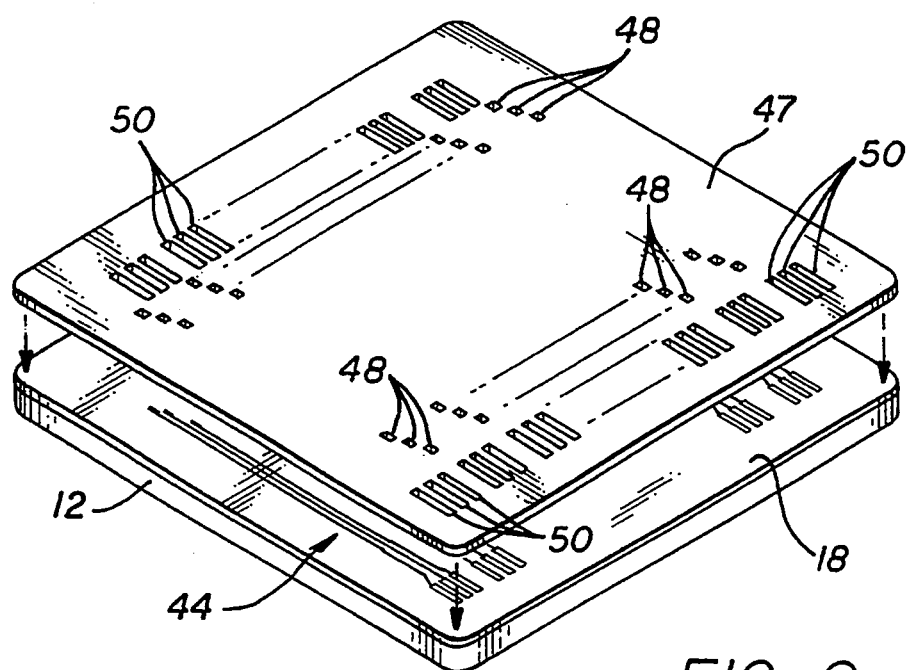
FIG. 9 is an exploded perspective view illustrating photoimaging steps for exposing portions of the conductive sensor traces.

FIG. 9 shows a contact mask 47 for placement over the cured cover layer 18. The contact mask 47 has apertures 48 and 50 formed therein through which the photoimagable layer 18 can be exposed to an appropriate light source. The thus-exposed cover layer 18 is subsequently processed to remove portions of the cover layer 18, resulting in the apertures 20 and 22 (FIG. 10) which respectively expose the distal end sensor tips and proximal end contact pads 26 of each sensor trace.

Appropriate electrode chemistries defining the distal end electrodes 24 can be applied to the sensor tips subsequent to exposure of the sensor tips through the apertures 20, or alternately before application of the cover layer 18. In this illustrative sensor embodiment for use as a glucose sensor, one of the sensor tips is coated with an electrode chemistry including glucose oxidase to defining a working electrode. The other two electrodes 24 may be coated with other suitable chemistries, or left uncoated, to define a reference electrode and a counter electrode for the electrochemical sensor.

Figure 11:
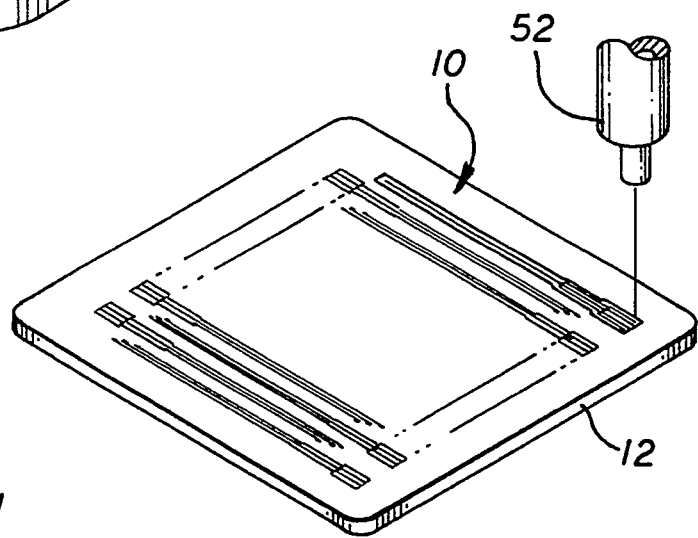
FIG. 11 is a perspective view illustrating removal of each finished sensor from the substrate.

The finished sensors 10 are quickly and easily removed from the substrate 12 by cutting along a line surrounding 11 each sensor on the substrate. FIG. 11 shows the cutting step to include a laser cutting device 52 used to cut through the base and cover layers 16, 18 along a line surrounding or circumscribing each sensor, in at least slight outward spaced relation from the conductive elements so that the sufficient interconnected base and cover layer material remains to seal the side edges of the finished sensor. Since the base layer 16 is not physically attached or adhered directly to the underlying substrate 12, the sensors 10 can be lifted quickly and easily from the substrate, without significant further processing steps or potential damage due to stresses incurred by physically pulling or peeling attached sensors from the substrate. The substrate 12 can thereafter be cleaned and reused, or otherwise discarded.

The present invention thus provides an improved sensor fabrication method wherein thin film flexible electrochemical sensors are formed on a flat substrate, without requiring direct physical adherence to or attachment of the sensors to the substrate.

A variety of modifications and improvements to the fabrication method of the present invention will be apparent to those skilled in the art. Accordingly, no limitation on the invention is intended by way of the foregoing description and accompanying drawings, except as set forth in the appended claims.

What is claimed is:

1. A method of making a thin film electrochemical sensor, said method comprising the steps of:
    applying a curable adhesive in a closed loop pattern to a flat surface of a rigid substrate;
    assembling a base layer of insulative sheet material with the substrate, with the adhesive interposed between the substrate and the base layer generally at the perimeter of the base layer, so that a shallow cavity is formed between the substrate and a central portion of the base layer;
    applying heat and pressure to the assembled base layer and substrate to expel air from the cavity and to position the central portion of the base layer in intimate surface contact with the substrate, and further to cure the adhesive to seal the cavity and thereby prevent air return flow into the cavity;
    forming at least one conductive sensor element on the base layer;
    forming a cover layer of insulative material to cover the at least one conductive sensor element and to extend beyond the marginal edges thereof in sealed contact with the base layer; and
    removing the sensor from the substrate by cutting through the cover and base layers along a line circumscribing and spaced outwardly from the at least one sensor element.

2. The method of claim 1 wherein said step of forming the at least one conductive sensor element comprises forming a plurality of conductive sensor elements on the base layer, said cover layer forming step comprising the step of forming the cover layer to cover said plurality of sensor elements and to extend beyond the marginal edges of each sensor element in sealed contact with the base layer, and further wherein said removing step comprises the step of cutting through the cover and base layers along a line circumscribing each sensor element.

3. The method of claim 1 wherein said sensor element forming step comprises photolithographic mask and etch steps.

4. The method of claim 1 further including the step of applying a selected electrode chemistry to said at least one conductive sensor element.

5. The method of claim 1 wherein the at least one conductive sensor element is elongated in shape, and further including the step of forming apertures in the cover layer to expose selected portions of the sensor element generally at opposite ends thereof.

6. The method of claim 1 wherein said cover layer forming step comprises the steps of applying insulative material in liquid form onto the base layer subsequent to said sensor trace forming step, spinning the substrate with the base layer thereon to form the liquid insulative material into a thin film, and curing the liquid insulative material to form the cover layer.

7. The method of claim 1 wherein said cover layer forming step comprises forming the cover layer from a photoimagable insulative material, and forming apertures in the cover layer to expose selected portions of the at least one sensor element by photomasking and removing portions of the cover layer.

8. The method of claim 1 wherein the base layer is polyimide sheet material.

9. The method of claim 1 wherein the central portion of the base layer is unattached to the substrate.

10. A method of making a thin film conductive sensor, said method comprising the steps of:
    assembling a base layer of insulative sheet material onto a flat surface of a rigid substrate;
    retaining at least a central portion of the base layer in intimate surface contact with the flat surface of the substrate, without directly attaching the central portion to the substrate;
    forming at least one conductive sensor element on the central portion of the base layer;
    forming a cover layer of insulative material to cover the at least one sensor element and to extend beyond the marginal edges thereof in sealed contact with the base layer;
    said sensor element forming step and said cover layer forming step being performed while the central portion of the base layer is retained in intimate surface contact with the flat surface of the substrate; and
    removing the sensor from the substrate by cutting through the cover and base layers along a line circumscribing and spaced outwardly from the at least one sensor element;
    said base layer assembling step comprising applying a curable adhesive in a closed loop pattern on the flat surface of the substrate, so that the adhesive is interposed between the substrate and the base layer generally at the perimeter of the base layer, and further wherein said retaining step comprises applying heat and pressure to the assembled base layer and substrate to press the central portion of the base layer into intimate surface contact with the substrate and to cure the adhesive.

11. The method of claim 10 wherein said retaining step comprises vacuum drawing the central portion of the base layer into intimate surface contact with the substrate.

12. The method of claim 10 wherein the at least one conductive sensor element is elongated in shape, and further including the step of forming apertures in the cover layer to expose selected portions of the sensor element generally at opposite ends thereof.

13. The method of claim 10 wherein the base layer is polyimide sheet material.

* * * * *